United States Patent
Lagrange

[11] Patent Number: 5,919,469
[45] Date of Patent: Jul. 6, 1999

[54] PRODUCTS DERIVED FROM 2-IMINO-2,3-DIHYDRO-1H-INDOLES, PROCESSES FOR THEIR PREPARATION, THEIR USE IN COSMETICS AND COSMETIC COMPOSITIONS USING THEM

[75] Inventor: Alain Lagrange, Coupvray, France

[73] Assignee: L'Oreal, Paris, France

[21] Appl. No.: 08/916,215

[22] Filed: Aug. 22, 1997

[30] Foreign Application Priority Data

Aug. 23, 1996 [FR] France .................................... 96 10411

[51] Int. Cl.$^6$ ...................................................... A61K 7/00
[52] U.S. Cl. ........................... 424/401; 548/455; 548/460; 548/469; 548/490; 548/491; 548/492; 424/59; 424/62; 424/63; 424/69; 424/70.6; 424/70.11; 528/422
[58] Field of Search ..................... 548/455, 460, 548/469, 490, 491, 492; 424/62, 63, 59, 69, 70.6, 70.11, 401; 528/422

[56] References Cited

U.S. PATENT DOCUMENTS

| | | | |
|---|---|---|---|
| 3,000,899 | 9/1961 | Hoffmann et al. | 260/319 |
| 3,944,672 | 3/1976 | Steinman | 424/274 |
| 3,984,563 | 10/1976 | Winters | 424/274 |
| 5,053,053 | 10/1991 | De Labbey et al. | 8/423 |
| 5,126,125 | 6/1992 | Pawelek | 424/62 |
| 5,178,637 | 1/1993 | Lagrange et al. | 8/405 |
| 5,354,870 | 10/1994 | Lang | 548/469 |
| 5,496,543 | 3/1996 | Lagrange et al. | 424/70.7 |
| 5,536,843 | 7/1996 | Knuebel et al. | 548/469 |
| 5,583,234 | 12/1996 | Lagrange et al. | 548/455 |
| 5,609,649 | 3/1997 | Junino et al. | 8/409 |

FOREIGN PATENT DOCUMENTS

| | | |
|---|---|---|
| 0 376 776 | 7/1990 | European Pat. Off. . |
| 0 428 441 | 5/1991 | European Pat. Off. . |
| 2 008 797 | 1/1970 | France . |
| 24 42 667 | 3/1975 | Germany . |
| 1 217 479 | 12/1970 | United Kingdom . |
| WO 92 17157 | 10/1992 | WIPO . |
| WO 93 13744 | 7/1993 | WIPO . |
| WO 93 13745 | 7/1993 | WIPO . |

OTHER PUBLICATIONS

Chemical Abstracts, vol. 79, No. 9, 1973 (abstract No. 53260x).
Chemical Abstracts, vol. 78, No. 11, 1973 (abstract No. 71606y).
Chemical Abstracts, vol. 87, No. 25, Dec. 19, 1977 (abstract No. 201378z).
Chemical Abstracts, vol. 94, No. 13, Mar. 30, 1981 (abstract No. 103110f).
Chemical Abstracts, vol. 75, No. 23, Dec. 6, 1971 (abstract No. 140696e).
Chemical Abstracts, vol. 74, No. 25, Jun. 21, 1971 (abstract No. 141438p).
Chemical Abstracts, vol. 73, No. 15, Oct. 12, 1970 (abstract No. 76975z).
Chemical Abstracts, vol. 88, No. 17, Apr. 24, 1978 (abstract No. 121064z).
Chemical Abstracts, vol. 73, No. 9, Aug. 31, 1970 (abstract No. 45252g).
Chemical Abstracts, vol. 68, No. 23, Jun. 3, 1968 (abstract No. 105143f).
Chemical Abstracts, vol. 79, No. 5, Aug. 6, 1973 (abstract No. 31782s).
Chemical Abstracts, vol. 93, No. 11. Sep. 15, 1980 (abstract No. 114247m).
Chemical Abstracts, vol. 90, No. 21, May 21, 1979 (abstract No. 168410r).
Chemical Abstracts, vol. 114, No. 13, Apr. 1, 1991 (abstract No. 121938t).
Chemical Abstracts, vol. 82, No. 23, Jun. 9, 1975 (abstract No. 156003g).

(List continued on next page.)

*Primary Examiner*—Samuel A. Acquah
*Attorney, Agent, or Firm*—Finnegan, Henderson, Farabow, Garrett & Dunner, L.L.P.

[57] ABSTRACT

Products derived from 2-imino-2,3-dihydro-1H-indoles resulting from the oxidative polymerization of at least one compound of formula (I) or (II) below:

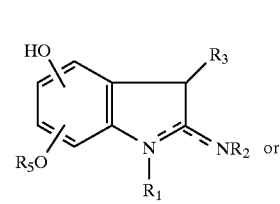

(I)

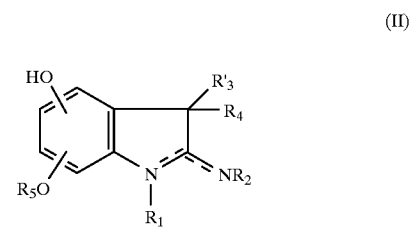

(II)

in which:

$R_1$, $R_2$ and $R_3$ denote hydrogen, alkyl, carboxyl, alkoxycarbonyl, monohydroxyalkyl, polyhydroxyalkyl, alkoxyalkyl, monoalkylaminoalkyl or dialkylaminoalkyl; $R'_3$ and $R_4$ denote alkyl, carboxyl, alkoxycarbonyl, monohydroxyalkyl, polyhydroxyalkyl, alkoxyalkyl, monoalkylaminoalkyl or dialkylaminoalkyl;

$R_5$ denotes hydrogen, alkyl, monohydroxyalkyl, polyhydroxyalkyl, alkoxyalkyl, monoalkylaminoalkyl or dialkylaminoalkyl;

and to the addition salts thereof with an acid, as well as to their uses in cosmetics for making up the exoskeleton and/or the skin.

34 Claims, No Drawings

OTHER PUBLICATIONS

Chemical Abstracts, vol. 80, No. 17, Apr. 29, 1974 (abstract No. 95788b).

Chemical Abstracts, vol. 108, No. 5, Feb. 1, 1988 (abstract No. 37569s).

Chemical Abstracts, vol. 107, No. 10, Sep. 7, 1987 (abstract No. 88896h).

Chemical Abstracts, vol. 119, No. 3, Jul. 19, 1993 (abstract No. 27959g).

Chemical Abstracts, vol. 123, No. 1, Jul. 3, 1995 (abstract No. 252s).

PRODUCTS DERIVED FROM 2-IMINO-2,3-DIHYDRO-1H-INDOLES, PROCESSES FOR THEIR PREPARATION, THEIR USE IN COSMETICS AND COSMETIC COMPOSITIONS USING THEM

The present invention relates to novel 2-imino-2,3-dihydro-1H-indole derivatives, to a process for their preparation, to their use in dyeing keratin fibres such as the hair and to dyeing processes using them.

The use of coloured pigments is of great value in the cosmetic field, in particular in products intended for making up the exoskeleton and/or the skin.

Inorganic pigments or pigments derived from synthetic direct dyes, or from pure carbon in the case of black pigments, are generally used. Depending on their applications, these various products have implementation problems and are not always free of compatibility and toxicology problems.

The inventor has now discovered novel products which may be used as pigments, in particular in cosmetics, these products being particularly advantageous in terms of the colorations which they make it possible to obtain, as well as in their cosmetic use.

The products in accordance with the invention are obtained by a process of oxidative polymerization using at least one 2-imino-2,3-dihydro-1H-indole.

For the purposes of analogy and simplicity, "indole product" or "indole polymer" will refer to the product obtained by oxidative polymerization of various compounds containing at least one 2-imino-2,3-dihydro-1H-indole.

The subject of the present invention is thus novel indole products as defined above.

Another subject of the invention relates to a product in the form of inorganic or organic particles containing, in or on the particles, an indole product as defined above.

Another subject of the invention relates to the process for the preparation of these products.

The subject of the invention is also the cosmetic application of these indole products, in particular in products for making up the skin and/or the exoskeleton, and in products intended for protecting the human epidermis against UV radiation.

The indole products in accordance with the invention result from the oxidative polymerization of at least one compound corresponding to formula (I) or to formula (II) below:

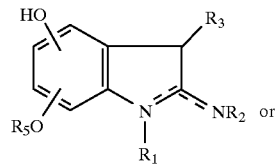

(I)

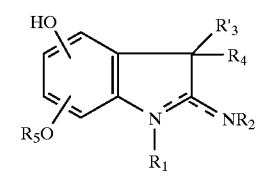

(II)

in which:
$R_1$, $R_2$ and $R_3$, which may be identical or different, denote a hydrogen atom or a $C_1$–$C_4$ alkyl, carboxyl, ($C_1$–$C_4$) alkoxycarbonyl, $C_1$–$C_4$ monohydroxyalkyl, $C_2$–$C_4$ polyhydroxyalkyl, ($C_1$–$C_4$)alkoxy($C_1$–$C_4$)alkyl, mono ($C_1$–$C_4$)alkylamino($C_1$–$C_4$)alkyl or di($C_1$–$C_4$) alkylamino($C_1$–$C_4$)alkyl radical;

$R'_3$ and $R_4$, which may be identical or different, denote a $C_1$–$C_4$ alkyl, carboxyl, ($C_1$–$C_4$)alkoxycarbonyl, $C_1$–$C_4$ hydroxyalkyl, $C_2$–$C_4$ polyhydroxyalkyl, ($C_1$–$C_4$) alkoxy($C_1$–$C_4$)alkyl, mono($C_1$–$C_4$)alkylamino($C_1$–$C_4$) alkyl or di($C_1$–$C_4$)alkylamino($C_1$–$C_4$)alkyl radical;

$R_5$ denotes a hydrogen atom or a $C_1$–$C_4$ alkyl, $C_1$–$C_4$ monohydroxyalkyl, $C_2$–$C_4$ polyhydroxyalkyl, ($C_1$–$C_4$)alkoxy($C_1$–$C_4$)alkyl, mono($C_1$–$C_4$)alkylamino ($C_1$–$C_4$)alkyl or di($C_1$–$C_4$)alkylamino($C_1$–$C_4$)alkyl radical; it being possible for the said alkyl or alkoxy radicals to be linear or branched.

The compounds of formulae (I) and (II) may also be in the form of an addition salt with an acid, and in particular in the form of hydrochlorides, hydrobromides, sulphates, tartrates, lactates or acetates.

Each of the formulae (I) and (II) defined above may give rise to several tautomeric forms, in which the preponderance and/or stability of each tautomeric form will depend on the nature of the various substituents $R_1$, $R_2$, $R_3$, $R'_3$ and $R_4$.

Formula (I) may give rise to the 3 tautomeric forms below:

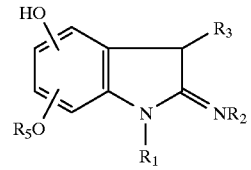

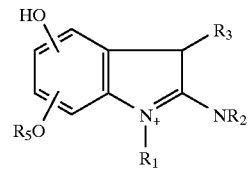

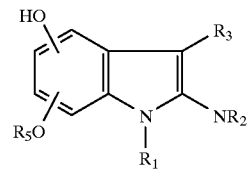

Formula (II) may give rise to the two tautomeric forms below:

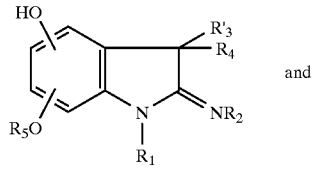

and

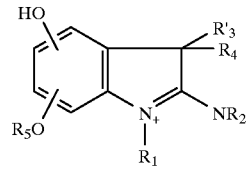

Among the preferred compounds of formulae (I) and (II), and the addition salts thereof with an acid, mention may be made more particularly of 5,6-dihydroxy-1,3-dihydroindol-2-ylideneamine, and the addition salts thereof with an acid.

The specific compounds of formula (IA) or (IIA) below, or the other tautomeric forms thereof:

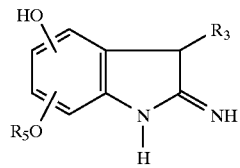

IA

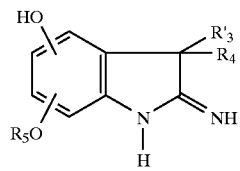

IIA in which $R_3$, $R'_3$, $R_4$ and R have the same meanings as those indicated above in the definitions of the formulae (I) and (II), may be obtained according to a process described in the R. G. Glushkov USSR patent 179 320 (1965) and in the document Chem. Abstr. 65, 2225 (1966), and corresponding to Schemes A and A' below:

Scheme A

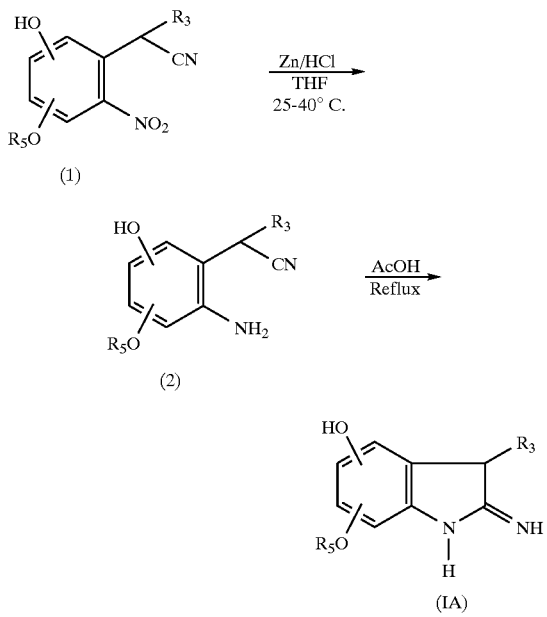

Scheme A'

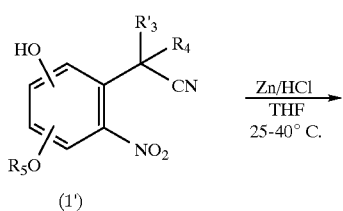

-continued

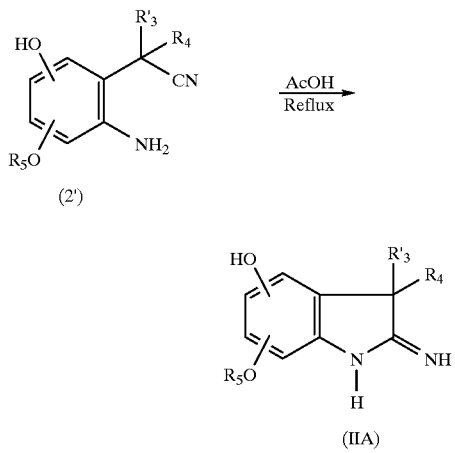

In Schemes A and A' defined above, the meanings of the radicals $R_3$, $R'_3$, $R_4$ and $R_5$ of formulae (1), (1'), (2) and (2') are identical to those indicated above in formulae (I) and (II).

This is a two-step process using starting compounds of formula (1) or (1') having the structure of the ortho-nitrophenylacetonitriles whose method of synthesis is known in the literature (M. Makosza, J. Winiarski, Acc. Chem. Res., 87, 1987, 282; M. Makosza, W. Danikiewicz, K. Wojciechowski; Liebigs Ann. Chem. 1988, 203).

The first step is either a chemical reduction in the presence of an organic solvent using metals such as zinc or tin, or a selective hydrogenation using a catalyst such as palladium or platinum. The solvents used are preferably ethers and more particularly tetrahydrofuran (THF). The reaction temperature ranges preferably from 25° C. to the reflux temperature of the solvent, and more particularly from 25 to 40° C.

The second step is a cyclization reaction in acidic medium, in the presence of an organic solvent. Acetic acid is preferably used. The reaction temperature is that of the refluxing solvent. The final product of formula (IA) or (IIA) is preferably isolated in the form of an addition salt with an acid. It is obtained by precipitation of the reaction medium in acidic medium. For example, in order to obtain a hydrochloride, a stream of HCl gas is passed through at the end of the reaction.

The specific compounds of formula (IB) or (IIB), corresponding respectively to the compounds of formula (I) and of formula (II) in which $R_1$ is a hydrogen atom, and the specific compounds of formula (IC) or (IIC) corresponding respectively to the compounds of formula (I) and of formula (II) in which $R_1$ and $R_2$ are both other than a hydrogen atom, may be obtained according to a preparation process, referred to in the

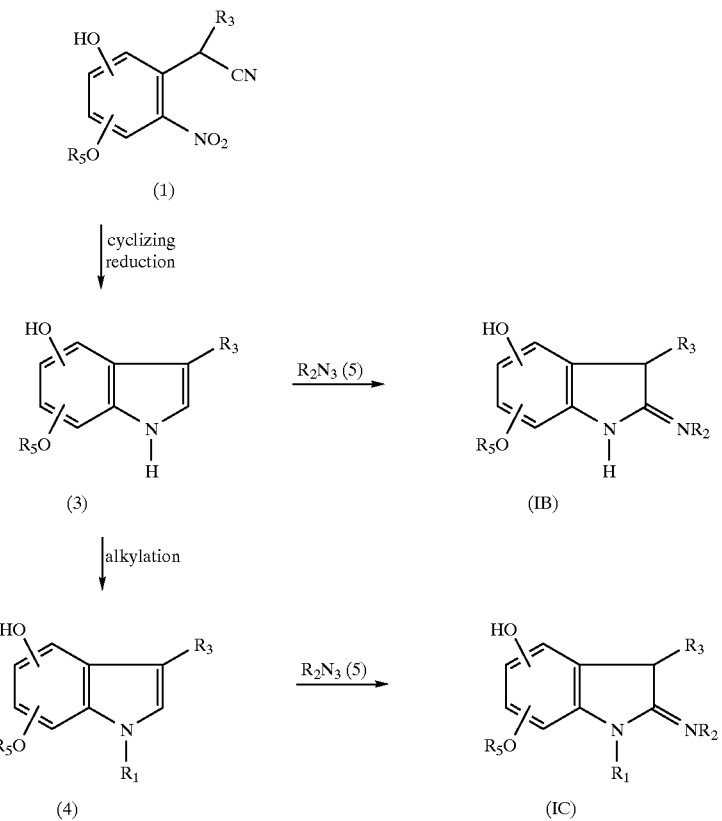
literature, and corresponding to Schemes B (above) and B' (below):
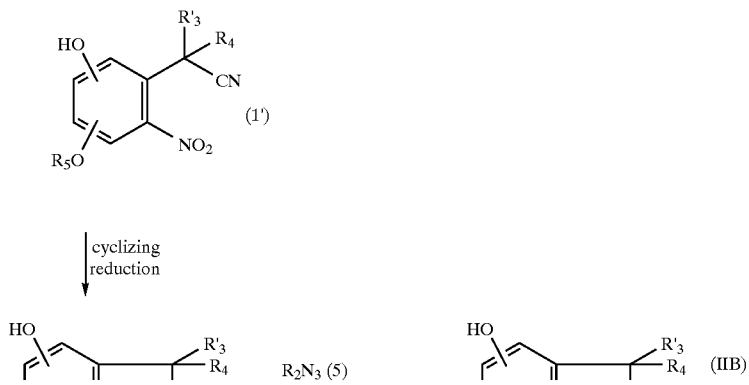

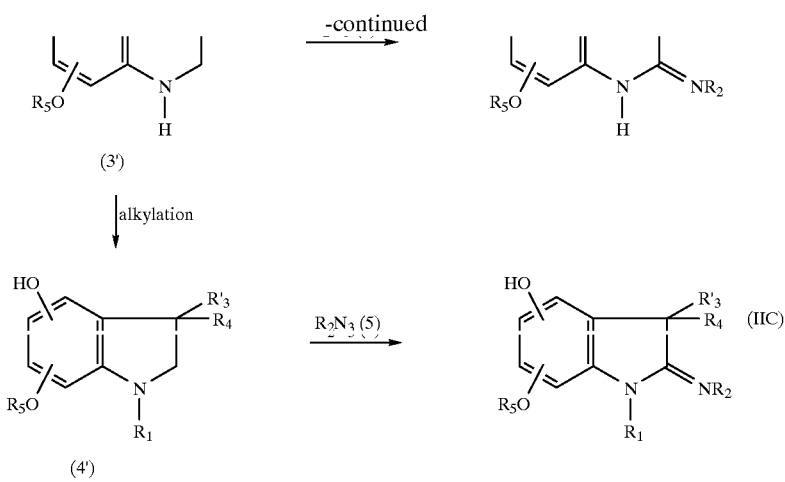

Compound (1) or (1') may be treated under cyclizing reduction conditions according to known methods such as, for example, that described by Makosza M. et al. in Liebigs Ann. Chem., 203, (1988) in order to lead respectively to the indole (3) or (3'). The indole (3) or (3') may be alkylated in order to lead respectively to the indole (4) or (4') according to standard methods described in "Heterocyclic compounds: Indoles" part II, pp. 72–73, published by N. J. Houlian, Wiley-Interscience.

The compounds (3) or (3') and (4) or (4') may react with an acid of structure (5) to lead respectively to the 2-iminoindolines (IB) or (IIB) and (IC) or (IIC) according to a method which has already been described [Harmon R. E. et al., J. Org. Chem. 38(1), 11, (1973)].

The compounds of structures (IB) or (IIB) and (IC) or (IIC) may also be obtained by reacting an amine $R_2NH_2$ with a 2-indolinethione derivative of structure (6) or (6') and (7) or (7') respectively as described by Hino T. et al. in Tetrahedron 27, 775, (1971) and represented in Schemes C and C' below:

Scheme C

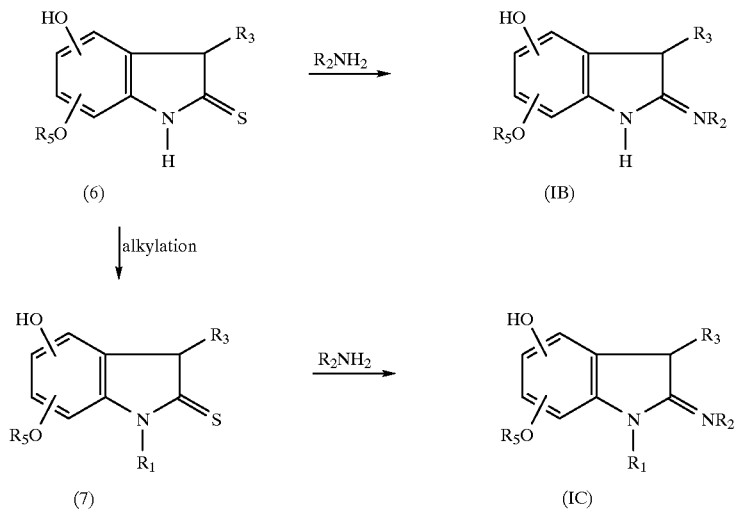

The indole products derived from 2-imino-2,3-dihydro-1H-indoles in accordance with the invention may also be obtained by co-oxidation of at least one compound of formula (I) or (II) defined above with at least one indole derivative and/or with at least one indoline derivative.

By way of indole derivative, mention may be made more particularly of the compounds corresponding to formula (III) below:

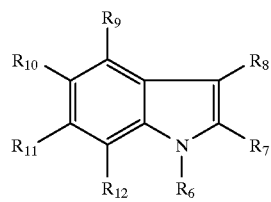

(III)

in which:
- $R_6$ and $R_8$, which may be identical or different, represent a hydrogen atom or a $C_1$–$C_4$ alkyl radical;
- $R_7$ represents a hydrogen atom or a $C_1$–$C_4$ alkyl, carboxyl or ($C_1$–$C_4$)alkoxycarbonyl radical;
- $R_9$ and $R_{12}$, which may be identical or different, represent a hydrogen atom or a hydroxyl, $C_1$–$C_4$ alkyl, amino, $C_1$–$C_4$ alkoxy, ($C_2$–$C_4$)acyloxy or ($C_2$–$C_4$)acylamino radical;
- $R_{10}$ represents a hydrogen or halogen atom or a hydroxyl, $C_1$–$C_4$ alkyl, $C_1$–$C_4$ alkoxy, amino, ($C_2$–$C_4$)acyloxy, ($C_2$–$C_4$)acylamino or trimethylsilyloxy radical;
- $R_{11}$ denotes hydrogen or a hydroxyl, ($C_1$–$C_4$)alkoxy, amino($C_2$–$C_4$)acyloxy, ($C_2$–$C_4$)acylamino, trimethylsiloxy or hydroxy($C_2$–$C_4$)alkylamino group;
- $R_{10}$ and $R_{11}$ may form, together with the carbon atoms to which they are attached, a methylenedioxy ring optionally substituted with a $C_1$–$C_4$ alkyl or $C_1$–$C_4$ alkoxy group or a carbonyldioxy ring;
- at least one of the groups $R_9$ to $R_{12}$ represents a group OZ or NHR, not more than one of the groups $R_9$ to $R_{12}$ denotes NHR; and not more than two of the groups $R_9$ to $R_{12}$ denote OZ, in the case where Z denotes hydrogen, these groups being in position 5 and 6; and at least one of the groups $R_9$ to $R_{12}$ represents hydrogen, in the case where only one of these groups denotes hydrogen, only one group from among $R_9$ to $R_{12}$ then denotes NHR or OZ, and the other groups denote $C_1$–$C_4$ alkyl; R denotes in NHR a hydrogen atom or a $C_2$–$C_4$ acyl or $C_2$–$C_4$ hydroxyalkyl group and Z denotes in OZ a hydrogen atom or a $C_2$–$C_{14}$ acyl, $C_1$–$C_4$ alkyl or trimethylsilyl group; and the corresponding salts.

The indole compounds of formula (III) are chosen in particular from 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-hydroxy-3-methylindole, 5-hydroxy-6-methoxy-2,3-dimethylindole, 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-N-β-hydroxyethylaminoindole, 4-aminoindole, 5-aminoindole, 6-aminoindole, 7-aminoindole, N-methyl-6-β-hydroxyethylaminoindole, 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole and 5,6-dimethoxyindole.

5,6-Dihydroxyindole, 6-hydroxyindole, 3-methyl-5,6-dihydroxyindole, 2-methyl-5,6-dihydroxyindole, 1-methyl-5,6-dihydroxyindole and 2-carboxy-5,6-dihydroxyindole, used alone or as a mixture, are preferred.

The indoline derivatives which are used in combination with the compounds of formula (I) or (II) in order to obtain the products in accordance with the invention are chosen in particular from the compounds of formula (IV) below:

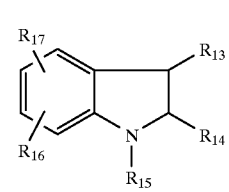

(IV)

in which:
- $R_{13}$ and $R_{15}$ represent, independently of each other, a hydrogen atom or a $C_1$–$C_4$ alkyl group;
- $R_{14}$ represents a hydrogen atom or a $C_1$–$C_4$ alkyl group or a carboxyl or a ($C_1$–$C_4$)alkoxycarbonyl group;
- $R_{16}$ denotes a hydrogen or halogen atom or a $C_1$–$C_4$ alkyl, hydroxyl, ($C_1$–$C_4$)alkoxyamino or $C_1$–$C_{10}$ alkylamino group;
- $R_{17}$ denotes a hydrogen atom or a hydroxyl, $C_1$–$C_4$ alkoxy or amino group; with the condition that at least one of the radicals $R_4$ or $R_5$ denotes a hydroxyl, alkoxy or amino group; and with the proviso that when $R_5$ denotes an amino group, $R_4$ cannot denote an alkylamino radical; $R_{16}$ and $R_{17}$ may also form a $C_1$–$C_2$ alkylenedioxy ring and are in position 5 and 6; as well as the corresponding salts.

The salts are cosmetically acceptable salts, in particular hydrochlorides, hydrobromides, sulphates and methanesulphonates. The hydrobromides of the above compounds are particularly preferred.

In the compounds of formula (IV), the $C_1$–$C_4$ alkyl radicals preferably denote methyl, ethyl, propyl, isopropyl, butyl or isobutyl. For the $C_1$–$C_{10}$ alkyl radicals, the $C_1$–$C_{10}$ alkyl radical preferably denotes methyl, ethyl, propyl, isopropyl, butyl, isobutyl, 1-methylhexyl, 1-methylheptyl or 1-methyloctyl, the alkoxy radicals preferably denote methoxy, ethoxy, propoxy and butoxy, and halogen denotes bromine, chlorine or iodine.

Among the compounds corresponding to formula (IV), the preferred compounds used in accordance with the invention are chosen from 5,6-dihydroxyindoline, 6-hydroxyindoline, 5,6-methylenedioxyindoline, 7-methoxy-6-hydroxyindoline, 6,7-dihydroxyindoline, 5-hydroxy-4-methoxyindoline, 4,5-dihydroxyindoline, 5-methoxy-6-hydroxyindoline, 4-hydroxy-5- methoxyindoline, 5-hydroxy-6-methoxyindoline, 4,7-dihydroxyindoline, 6-aminoindoline, N-ethyl-4-hydroxyindoline, 1-ethyl-6-aminoindoline, 5,6-diaminoindoline, 1-methyl-6-aminoindoline, 2-methyl-6-aminoindoline, 3-methyl-6-aminoindoline, 2-methyl-5,6-diaminoindoline, 5-chloro-7-aminoindoline, 3-methyl-5,7-diaminoindoline, 5,7-diaminoindoline, 2-methyl-5,7-diaminoindoline, 7-aminoindoline, 2-methyl-7-aminoindoline, 4-aminoindoline, 4-amino-6-chloroindoline, 4-amino- 6-iodoindoline, 4-amino-5-bromoindoline, 4-amino-5-hydroxyindoline, 4-amino-7-hydroxyindoline, 4-amino-5-methoxyindoline, 4-amino-6-methoxyindoline, 5-aminoindoline, 2,3-dimethyl-5-aminoindoline, 1-methyl-5-aminoindoline, 2-methyl-5-aminoindoline, 5-N-(1-methylhexyl)-aminoindoline, 5,6-dimethoxyindoline and 5,6-dihydroxy-2-carboxyindoline.

When the products derived from 2-imino-2,3-dihydro-1H-indoles in accordance with the invention may be prepared by co-oxidation, up to 50 mol % of indole derivative and/or of indoline derivative relative to the total number of moles of derivatives of formula (I) or (II) to be oxidized may preferably be used.

The products derived from 2-imino-2,3-dihydro-1H-indoles in accordance with the invention may be prepared according to various oxidative polymerization processes.

According to a first type of process, a simple atmospheric oxidation is carried out. In this case, no oxidizing agent other than atmospheric air is used and the process is preferably performed at an alkaline pH in a water or water/solvent medium.

The atmospheric oxidation may also be carried out in the presence of an alkaline agent and/or a metal catalyst for oxidation such as the cupric ion.

According to a second type of process, the products in accordance with the invention may be prepared in the presence of an oxidizing agent such as hydrogen peroxide, peracids and persalts.

Among the peracids and persalts, mention may be made of periodic acid and its water-soluble salts, permanganates and dichromates, such as those of sodium or of potassium, ammonium persulphate and organic peracids.

The periodic acid salt preferred is sodium periodate.

Other oxidizing agents are chosen from alkali metal chlorites, silver oxide, ferric chloride, lead oxide, sodium nitrite and rare-earth metal salts, in particular such as the cerium salt.

Organic oxidizing agents chosen from ortho- and para-benzoquinones, ortho- and para-benzoquinone monoimines and diimines, 1,2- and 1,4-naphthoquinones and 1,2- and 1,4-naphthoquinone mono- or diimines may also be used.

Lastly, the oxidation may be carried out using iodide such as an alkali-metal, alkaline-earth metal or ammonium iodide in the presence of hydrogen peroxide.

These oxidizing agents may optionally be activated by a pH modifier and/or by a metal oxidation catalyst.

The oxidation is generally carried out within a temperature range extending from room temperature to 100° C., with a preference for temperatures ranging from 20 to 80° C.

It is generally possible to form the indoline products in accordance with the invention by enzymatic oxidation. This oxidation is carried out in an oxidizing medium and in the presence of an enzyme with oxidizing or peroxidizing activity, such as enzymes chosen from horseradish peroxidase, chloroperoxidase, milk peroxidase and cytochrome C peroxidase, as well as products having a similar activity, that of peroxidizing enzymes such as haemoglobin, methaemoglobin, myoglobin and methmyoglobin.

For the products intended for cosmetic application, hydrogen peroxide, periodic acid and its salts, potassium permanganate, sodium hypochlorite, ammonium persulphate, sodium nitrite and the iodide/hydrogen peroxide system are preferably used as oxidizing agents. When an iodide is used in the presence of aqueous hydrogen peroxide solution, it is preferably sodium or potassium iodide at a weight concentration ranging from 1 to 6% relative to the weight of the reaction medium.

The order of addition of the compounds involved in the preparation of the product in accordance with the invention is unimportant on condition that the oxidizing agent is added last when it is used without a pH modifier and, in the case of the iodide/hydrogen peroxide oxidizing system, either the hydrogen peroxide or the iodide is added last.

In the case where a pH modifier is used to activate the oxidizing agent, it is preferred to add either the oxidizing agent or the pH modifier last.

The pH modifiers are acidifying or basifying agents usually used in cosmetics.

Before using the oxidizing agent, the derivative to be oxidized is dissolved in aqueous solution or in a water/solvent medium with a proportion of solvent ranging from 0.5 to 95% or in a pure solvent medium.

The solvents are preferably chosen from $C_1$–$C_4$ lower alcohols such as ethyl alcohol, propyl or isopropyl alcohol, tert-butyl alcohol, alkylene glycols such as ethylene glycol, propylene glycol, alkylene glycol alkyl ethers such as ethylene glycol monomethyl, monoethyl and monobutyl ethers, propylene glycol monomethyl ether, dipropylene glycol monomethyl ether and methyl lactate.

These solvents must moreover be able to dissolve the compound of formula (I) or (II) and possibly the indoline derivative and/or the indole derivative used to form the final product in accordance with the invention. The preferred solvent is ethanol and the preferred oxidation medium is aqueous-alcoholic with an ethanol content ranging from 1 to 15%.

In the process in accordance with the invention, the derivatives to be oxidized generally represent from 0.1 to 30% and preferably from 1 to 20% by weight relative to the total weight of the reaction medium.

The contact times between the derivatives to be oxidized and the oxidizing reagents may range from a few minutes to a few days depending on the processes.

The preferred alkaline agents are sodium hydroxide, alkaline carbonates or aqueous ammonia. When they are used, their concentration in the oxidation medium preferably ranges from $5 \times 10^{-4}$ to 10% by weight.

In order to prepare the products in accordance with the invention, the process of oxidation with aqueous hydrogen peroxide solution in the presence of aqueous ammonia is preferably used.

When the oxidation process is complete, the coloured indoline product thus formed is isolated by means such as filtration, centrifugation or freeze-drying. In order to eliminate the traces of derivatives to be oxidized that have not reacted, the product is rinsed thoroughly with water before or after filtration or centrifugation.

In the case where the product in accordance with the invention is prepared by simple atmospheric oxidation, it is preferred to isolate the indoline product by freeze-drying.

In order to obtain a homogeneous product of sufficiently fine particle size, it is then possible to treat the product obtained with standard grinding systems via a dry or wet route. A micronization process may also be used.

The particle size of the final product is preferably such that the average particle diameter is less than 50 microns and preferably less than 20 microns.

Similarly, 90% of the particles preferably have a diameter generally less than 100 microns and more preferably less than 50 microns.

The products derived from 2-imino-2,3-dihydro-1H-indoles in accordance with the invention are essentially polymers that are generally insoluble in the cosmetic media usually used. However, these products may be used in solution in specific solvent media, for example using a medium whose pH is high.

The products derived from 2-imino-2,3-dihydro-1H-indoles in accordance with the invention may, according to a particular mode of the invention, be used in the form of a powder containing inorganic or organic particles in which the largest size is less than 20 microns and containing, in and/or on the particles, the products in accordance with the invention formed in situ by oxidative polymerization of at least one compound of formula (I) or (II) as defined above.

The powders containing the products derived from 2-imino-2,3-dihydro-1H-indoles in accordance with the invention constitute another subject of the invention.

The inorganic or organic particles contained in the pigmentary powders in accordance with the invention are those used in the pigmentary powders described in application EP-A-0,575,605.

The powders in accordance with the invention are prepared according to the various types of process described in application EP-A-0,575,605, the disclosure of which is specifically incorporated herein by reference.

Another subject of the invention relates to the use of these powders in, and for the preparation of, cosmetic or dermatological compositions, in particular in any product to treat or care for the skin and/or the exoskeleton. The term "exoskeleton" refers to head hair, body hair, the eyelashes, the eyebrows and the nails.

According to one subject of the invention, the indole products in accordance with the invention may be used in cosmetics or dermatology, in particular in any product to treat or care for the skin and/or the exoskeleton.

In their cosmetic application, the indole products in accordance with the invention are used in free form or are incorporated in powders based on inorganic or organic particles, in cosmetic compositions containing a cosmetically acceptable medium, at a concentration preferably ranging from 0.1 to 35% by weight and in particular from 0.5 to 20% by weight relative to the total weight of the composition.

These compositions may be used as make-up products, in particular for the eyelashes, the eyebrows, the skin or the nails, such as in the form of eyeshadows, blushers, eyeliners, mascaras for the eyelashes and the eyebrows, and nail varnishes, or as dye compositions for the hair, in particular in order to carry out a temporary dyeing of the hair or make-up.

These compositions may also be used for protecting the human epidermis against UV radiation.

The compositions may be in the form of a lotion, a thickened lotion, a gel, a cream, a milk, a powder or a stick and may optionally be packaged as an aerosol and be in the form of a mousse or a spray.

When the compositions are used for making up the skin, the eyelashes and the eyebrows, they may, in particular, be in solid or pasty, anhydrous or aqueous form, such as oil-in-water or water-in-oil emulsions or alternatively suspensions.

These compositions have the advantage of being particularly stable and of having a good level of harmlessness.

When the compositions are used for protecting the human epidermis against UV radiation, they constitute so-called "antisun" compositions and they may be in the form of suspensions or dispersions in solvents or fatty substances, or alternatively in the form of emulsions such as creams and milks, ointments, gels, solid tubes or aerosol mousses.

When they are used in the form of emulsions, they may also contain surfactants that are well known in the state of the art, such as anionic, nonionic, cationic or amphoteric surfactants.

The make-up compositions and the antisun compositions may also contain fatty substances, organic solvents, silicones, thickeners, softeners, sunscreens, antifoaming agents, moisturizers, fragrances, preserving agents, antioxidants, fillers, sequestering agents, treating agents such as anionic, cationic, nonionic or amphoteric polymers or mixtures thereof, propellants and acidifying or basifying agents.

The fatty substances may contain an oil or a wax or a mixture thereof, fatty acids, fatty alcohols, petroleum jelly, paraffin, lanolin, hydrogenated lanolin or acetylated lanolin.

The oils are chosen from animal, plant, mineral or synthetic oils and, in particular, hydrogenated palm oil, hydrogenated castor oil, liquid petroleum jelly, liquid paraffin and liquid purcellin.

The waxes are chosen from animal, fossil, plant, mineral or synthetic waxes. Mention may be made in particular of beeswaxes, carnauba wax, candelilla wax, sugar cane wax, Japan wax, ozokerites, Montan wax, microcrystalline waxes and paraffin waxes.

The compositions in accordance with the invention may also contain, in addition to the indoline products as defined above, pigments generally used in cosmetics, in particular pearly and/or pearlescent pigments which make it possible to vary the colorations that may be obtained, or to increase the protection against ultraviolet radiation. In the latter case, pigments or nanopigments of metal oxides such as titanium oxide, zinc oxide, cerium oxide or zirconium oxide are used more particularly.

The nanopigments which are preferably used are pigments having an average diameter of less than 100 nm and preferably from 5 to 50 nm. They may be coated or uncoated.

The coated pigments are pigments which have undergone one or more surface treatments of chemical, electronic, mechanochemical and/or mechanical nature with compounds as described, for example, in Cosmetics and Toiletries, February 1990, Vol. 105, pages 53–64, such as amino acids, beeswax, fatty acids, fatty alcohols, anionic surfactants, lecithins, sodium, potassium, zinc, iron or aluminium salts of fatty acids, metal (titanium or aluminium) alkoxides, polyethylene, silicones, proteins (collagen, elastin), alkanolamines, silicon oxides, metal oxides or sodium hexametaphosphate.

When they are used for the temporary dyeing of the hair, they are in the form of relatively thickened lotions, a gel, a mousse or a spray containing the indoline products in an aqueous or water/solvent(s) medium in the proportions indicated above.

When they are used for treating the nails, the indoline product is introduced into a nail varnish medium comprising a volatile solvent and polymers.

Another subject of the invention relates to the process for the temporary dyeing of the hair, for making up the skin and the exoskeleton, or for protecting the human epidermis against the harmful effects of UV radiation, using the indoline products according to the invention.

These products may be applied directly in powder form or by means of cosmetic compositions as defined above.

The examples which follow are intended to illustrate the invention without, however, being limiting in nature.

PREPARATION EXAMPLES

Example 1

6.62 g (0.033 mol) of 5,6-dihydroxy-1,3-dihydroindol-2-ylideneamine hydrochloride were dissolved in 50 ml of aqueous 0.1% ammonia solution. This solution was brought to 80° C. and 3 ml of aqueous 20% ammonia solution (0.033 mol) were added. 7.65 g of aqueous hydrogen peroxide solution containing 0.675 mol of hydrogen peroxide were added to this mixture while maintaining the temperature from 80 to 85° C. Once the addition was complete, the temperature was maintained at 80° C. for 2.5 hours and the reaction medium was then cooled. The product was centrifuged at 500 revolutions/minute for 10 minutes and taken up in 250 ml of water and then centrifuged at 500 revolutions/minute for 10 minutes; this operation was repeated three times. After drying, 3.1 g of dark brown powder were obtained. This powder could then be micronized according to the standard micronization processes. In a variant of this process, the product before drying was passed in wet medium into a ball mill.

Example 2

5.958 g (0.0297 mol) of 5,6-dihydroxy-1,3-dihydroindol-2-ylideneamine hydrochloride and 0.492 g (0.0033 mol) of 5,6-dihydroxyindole were dissolved in 50 ml of aqueous 0.1% ammonia solution. This mixture was brought to 80° C. and 2.7 ml of aqueous 20% ammonia solution (0.0297 mol) were then added. 28.8 g of aqueous hydrogen peroxide solution containing 0.033 mol of hydrogen peroxide were added to this mixture over 2 h 30 minutes while maintaining the temperature from 80° to 85° C. Once the addition was complete, the temperature was maintained at 80° C. for 3 hours and the reaction medium was then cooled. The black product was drained off and washed with water. After drying, 4.6 g of black powder were obtained, which could be micronized as in Example 1. The black product obtained before drying could, as in Example 1, be passed in wet medium in a ball mill.

FORMULATION EXAMPLE

Example A

An anhydrous mascara having the composition below was prepared:

Carnauba wax 5.0 g
Candelilla wax 5.0 g
Ethanol 3.0 g
Montmorillonite modified with an organic substance 4.0 g
Lanolin 2.0 g
Talc 10.0 g
Black powder of Example 1 2.0 g
Isoparaffin qs 100 g This waterproof mascara is black in colour.

We claim:

1. An indole product derived from 2-imino-2,3-dihydro-1H-indoles wherein said product results from the oxidative polymerization of at least one compound of formula (I) or (II) below or of at least one acid addition salt thereof:

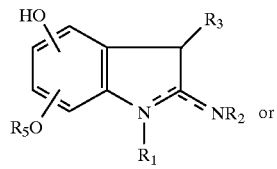
(I)

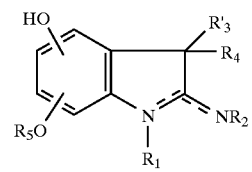
(II)

wherein:

$R_1$, $R_2$ and $R_3$, which may be identical or different, denote a hydrogen atom or a $C_1$–$C_4$ alkyl, carboxyl, $(C_1$–$C_4)$ alkoxycarbonyl, $C_1$–$C_4$ monohydroxyalkyl, $C_2$–$C_4$ polyhydroxyalkyl, $(C_1$–$C_4)$alkoxy$(C_1$–$C_4)$alkyl, mono$(C_1$–$C_4)$alkylamino$(C_1$–$C_4)$alkyl or di$(C_1$–$C_4)$ alkylamino$(C_1$–$C_4)$alkyl radical;

$R'_3$ and $R_4$, which may be identical or different, denote a $C_1$–$C_4$ alkyl, carboxyl, $(C_1$–$C_4)$alkoxycarbonyl, $C_1$–$C_4$ monohydroxyalkyl, $C_2$–$C_4$ polyhydroxyalkyl, $(C_1$–$C_4)$alkoxy$(C_1$–$C_4)$alkyl, mono$(C_1$–$C_4)$alkylamino $(C_1$–$C_4)$alkyl or di$(C_1$–$C_4)$alkylamino$(C_1$–$C_4)$alkyl radical;

$R_5$ denotes a hydrogen atom or a $C_1$–$C_4$ alkyl, $C_1$–$C_4$ monohydroxyalkyl, $C_2$–$C_4$ polyhydroxyalkyl, $(C_1$–$C_4)$ alkoxy$(C_1$–$C_4)$alkyl, mono$(C_1$–$C_4)$alkylamino$(C_1$–$C_4)$ alkyl or di$(C_1$–$C_4)$alkylamino$(C_1$–$C_4)$alkyl radical; wherein said alkyl or alkoxy radicals may be linear or branched.

2. An indole product according to claim 1 wherein said at least one acid addition salt is selected from hydrochlorides, hydrobromides, sulphates, tartrates, lactates and acetates.

3. An indole product resulting from the oxidative polymerization of 5,6-dihydroxy-1,3-dihydroindol-2-ylideneamine or of at least one acid addition salt thereof.

4. An indole product according to claim 1 wherein said product results from the co-oxidation of at least one compound of formula (I) or (II) with at least one compound selected from indole derivatives and indoline derivatives.

5. An indole product according to claim 4 wherein said indole derivatives correspond to formula (III) below or to the corresponding salts:

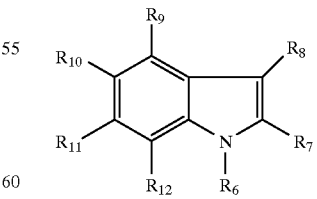
(III)

wherein:

$R_6$ and $R_8$, which may be identical or different, represent a hydrogen atom or a $C_1$–$C_4$ alkyl radical;

$R_7$ represents a hydrogen atom or a $C_1$–$C_4$ alkyl, carboxyl or $(C_1$–$C_4)$alkoxycarbonyl radical;

$R_9$ and $R_{12}$, which may be identical or different, represent a hydrogen atom or a hydroxyl, $C_1$–$C_4$ alkyl, amino, $C_1$–$C_4$ alkoxy, ($C_2$–$C_4$)acyloxy or ($C_2$–$C_4$)acylamino radical;

$R_{10}$ represents a hydrogen or halogen atom or a hydroxyl, $C_1$–$C_4$ alkyl, $C_1$–$C_4$ alkoxy, amino, ($C_2$–$C_4$)acyloxy, ($C_2$–$C_4$)acylamino or trimethylsilyloxy radical; and $R_{11}$ represents hydrogen or a hydroxyl, ($C_1$–$C_4$)alkoxy, amino($C_2$–$C_4$)acyloxy, ($C_2$–$C_4$)acylamino, trimethylsiloxy or hydroxy($C_2$–$C_4$)alkylamino group;

with the proviso that:

$R_{10}$ and $R_{11}$ may also form, together with the carbon atoms to which they are attached, a methylenedioxy ring optionally substituted with a $C_1$–$C_4$ alkyl or $C_1$–$C_4$ alkoxy group or a carbonyldioxy ring;

at least one of the groups $R_9$ to $R_{12}$ represents a group OZ or NHR, not more than one of the groups $R_9$ to $R_{12}$ denotes NHR, and not more than two of the groups $R_9$ to $R_{12}$ denote OZ, in the case where Z denotes hydrogen, these groups being in position 5 and 6; and at least one of the groups $R_9$ to $R_{12}$ represents hydrogen, in the case where only one of these groups denotes hydrogen, only one group from among $R_9$ to $R_{12}$ then denotes NHR or OZ, and the other groups denote $C_1$–$C_4$ alkyl;

wherein R denotes in NHR a hydrogen atom or a $C_2$–$C_4$ acyl or $C_2$–$C_4$ hydroxyalkyl group and Z denotes in OZ a hydrogen atom or a $C_2$–$C_{14}$ acyl, $C_1$–$C_4$ alkyl or trimethylsilyl group.

6. An indole product according to claim 4 wherein said indoline derivatives correspond to formula (IV) below or to the corresponding salts:

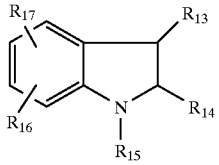

(IV)

wherein:

$R_{13}$ and $R_{15}$, which may be identical or different, represent a hydrogen atom or a $C_1$–$C_4$ alkyl group;

$R_{14}$ represents a hydrogen atom or a $C_1$–$C_4$ alkyl group or a carboxyl or a ($C_1$–$C_4$)alkoxycarbonyl group;

$R_{16}$ represents a hydrogen or halogen atom or a $C_1$–$C_4$ alkyl, hydroxyl, ($C_1$–$C_4$)alkoxyamino or $C_1$–$C_{10}$ alkylamino group; and $R_{17}$ represents a hydrogen atom or a hydroxyl, $C_1$–$C_4$ alkoxy or amino group;

with the proviso that:

at least one of the radicals $R_4$ or $R_5$ denotes a hydroxyl, alkoxy or amino group;

when $R_5$ denotes an amino group, $R_4$ cannot denote an alkylamino radical; and $R_{16}$ and $R_{17}$ may also form a $C_1$–$C_2$ alkylenedioxy ring and are in position 5 and 6.

7. An indole product according to claim 4 wherein said co-oxidation uses up to 50 mol % of said at least one compound selected from indole derivatives and indoline derivatives relative to the total number of moles of compounds of formula (I) or (II) to be oxidized.

8. A process for the preparation of a product according to claim 1 wherein atmospheric oxidation is carried out.

9. A process according to claim 8 wherein said atmospheric oxidation is carried out in the presence of an alkaline agent and/or of a metal oxidation catalyst.

10. A process for the preparation of a product according to claim 1 wherein said product is prepared by oxidation in the presence of an oxidizing agent, and in the presence or absence of a pH modifier and/or of a metal oxidation catalyst.

11. A process according to claim 10 wherein said oxidizing agent is selected from hydrogen peroxide, peracids, persalts, alkaline chlorites, silver oxide, ferric chloride, lead oxide, sodium nitrite and rare-earth metal salts.

12. A process according to claim 10, wherein said oxidizing agent is an ortho- or para-benzoquinone, an ortho- or para-benzoquinone monoimine or diimine, a 1,2- or 1,4-naphthoquinone, or a 1,2- or 1,4- naphthoquinone mono- or diimine.

13. A process according to claim 11 wherein the oxidation is carried out using, in a first stage, either an alkali-metal, alkaline-earth metal or ammonium iodide and, in a second stage, hydrogen peroxide.

14. A process according to claim 11 wherein the oxidation is carried out using, in a first stage, hydrogen peroxide, followed, in a second stage, by the addition of an alkali-metal, alkaline-earth metal or ammonium iodide.

15. A process for the preparation of a product according to claim 1 wherein the oxidation is carried out enzymatically.

16. A process according to claim 10 wherein said oxidation is carried out by introducing at least one compound of formula (I) or (II) into aqueous solution or into a water/solvent medium or into a pure solvent medium, optionally with at least one compound selected from indoles and indolines, and thereafter the oxidizing agent is added in amounts which are sufficient to form the indole product.

17. A process according to claim 16 wherein said solvent is selected from $C_1$–$C_4$ lower alcohols, alkylene glycols, alkylene glycol alkyl ethers and methyl lactate.

18. A process according to claim 8, wherein said at least one compound of formula (I) or (II) and optionally at least one compound selected from indoles and indolines represents from 0.1 to 30% by weight relative to the total weight of the reaction medium.

19. An indole product according to claim 1 wherein said product is isolated in the form of particles having an average particle size of less than 50 microns.

20. An indole product according to claim 19 wherein said average particle size is 20 microns.

21. A product in powder form comprising particles wherein said particles are inorganic or organic particles less than 20 microns in size and further comprising, in and/or on the particles, at least one indole product according to claim 1.

22. A process comprising the step of including a product according to claim 21 in a composition to form a cosmetic or dermatological composition.

23. A process comprising the step of including at least one indole product according to claim 1 in a cosmetic or dermatological composition.

24. A cosmetic or dermatological composition wherein said composition comprises at least one indole product according to claim 1.

25. A cosmetic or dermatologic composition according to claim 24 wherein said at least one indole product is present in a concentration ranging from 0.1 to 35% by weight relative to the total weight of the composition.

26. A cosmetic or dermatological composition according to claim 24 wherein said composition further comprises a cosmetically acceptable medium.

27. A composition according to claim 24 wherein said composition is in the form of a thickened lotion, a gel, a cream, a milk, a powder or a stick, or optionally packaged as an aerosol in the form of a spray or a mousse.

28. A composition according to claim 24 wherein said composition is intended to be used for making up the skin, the nails, the eyelashes and the eyebrows, and further wherein said composition is in liquid, solid or pasty, anhydrous or aqueous form.

29. A composition according to claim 24 wherein said composition is intended for protecting the human epidermis against UV radiation, and further wherein said composition is in the form of a suspension or dispersion in solvents or fatty substances or in the form of an emulsion, an ointment, a gel, a solid tube or an aerosol mousse.

30. A composition according to claim 24 wherein said composition further comprises at least one ingredient selected from fatty substances, organic solvents, silicones, thickeners, softeners, surfactants, sunscreens, antifoaming agents, moisturizers, fragrances, preserving agents, antioxidants, fillers, sequestering agents, treating agents, propellants, acidifying and basifying agents and other pigments.

31. A process for the temporary dyeing of the hair comprising the step of applying at least one composition according to claim 24 to said hair.

32. A process for making up the skin or the exoskeleton comprising the step of applying at least one composition according to claim 24 to said skin or exoskeleton.

33. A process according to claim 10, wherein said at least one compound of formula (I) or (II) and optionally at least one compound selected from indoles and indolines represents from 0.1 to 30% by weight relative to the total weight of the reaction medium.

34. A process according to claim 15, wherein said at least one compound of formula (I) or (II) and optionally at least one compound selected from indoles and indolines represents from 0.1 to 30% by weight relative to the total of the reaction medium.

* * * * *